United States Patent [19]

Fischer et al.

[11] Patent Number: 4,985,063
[45] Date of Patent: Jan. 15, 1991

[54] 3-ARYL-PYRROLIDINE-2,4-DIONES

[75] Inventors: Reiner Fischer, Monheim; Hermann Hagemann, Leverkusen; Andreas Krebs, Odenthal-Holz; Albrecht Marhold, Leverkusen; Klaus Lürssen; Robert R. Schmidt, both of Bergisch-Gladbach; Hans-Joachim Santel, Leverkusen; Benedikt Becker, Mettmann; Klaus Schaller; Wilhelm Stendel, both of Wuppertal, all of Fed. Rep. of Germany

[73] Assignee: Bayer Aktiengesellschaft, Leverkusen, Fed. Rep. of Germany

[21] Appl. No.: 391,227

[22] Filed: Aug. 8, 1989

[30] Foreign Application Priority Data

Aug. 20, 1988 [DE] Fed. Rep. of Germany ....... 3828404
Sep. 20, 1988 [DE] Fed. Rep. of Germany ....... 3831852
Apr. 26, 1989 [DE] Fed. Rep. of Germany ....... 3913682

[51] Int. Cl.$^5$ ................. C07D 471/02; C07D 487/04; A61K 31/485; A61K 31/40
[52] U.S. Cl. .......................... 71/88; 71/90; 71/92; 71/94; 71/95; 514/183; 514/214; 514/256; 514/299; 514/339; 514/365; 514/406; 514/407; 514/413; 540/476; 540/593; 540/450; 540/610; 546/183; 546/272; 546/326; 548/181; 548/333; 548/453; 548/533; 548/374; 544/333
[58] Field of Search ............... 540/593, 476; 546/183, 546/272; 548/453, 181, 374; 71/88, 94, 95, 90, 92; 514/183, 214, 299, 413; 544/333

[56] References Cited

U.S. PATENT DOCUMENTS 3,274,202  9/1966  Mohrbacher ...................... 546/183

FOREIGN PATENT DOCUMENTS 0262399  4/1988  European Pat. Off. .
0259993  9/1988  Fed. Rep. of Germany .

OTHER PUBLICATIONS

Schmierer Chemical Abstracts, vol. 103, 377 21g, Aug. 5, 1985.

*Primary Examiner*—Mark L. Berch

*Attorney, Agent, or Firm*—Sprung Horn Kramer & Woods

[57] ABSTRACT

A 3-aryl-pyrrolidine-2,4-dione (e) derivative of the formula (I)

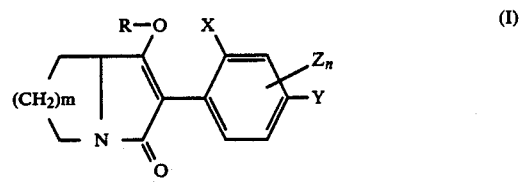

in which
X represents alkyl, halogen and alkoxy,
Y represents hydrogen, alkyl, halogen, alkoxy and halogenoalkyl,
Z represents alkyl, halogen and alkoxy,
m represents a number from 1-4,
n represents a number from 0-3, R represents hydrogen,

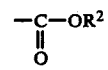

or A where
A represents a metal cation equivalent or represents an ammonium ion,
$R^1$ represents optionally halogen-substituted alkyl, alkenyl, alkoxyalkyl, alkylthioalkyl, polyalkoxyalkyl and optionally substituted cycloalkyl which can be interrupted by hetero atoms, or represents optionally substituted phenyl, optionally substituted phenylalkyl, substituted hetaryl, substituted phenoxyalkyl and substituted hetaryloxyalkyl and
$R^2$ represents optionally halogen-substituted alkyl, cycloalkyl, alkenyl, alkoxyalkyl, polyalkoxyalkyl and optionally substituted phenyl, as well as the pure enantiomeric forms of compounds of the formula (I). The compounds of formula (I) are effective as insecticidal, acaricidal, herbicidal and antimycotic agents.

6 Claims, No Drawings

3-ARYL-PYRROLIDINE-2,4-DIONES

The invention relates to new 3-aryl-pyrrolidine-2,4-dione (e) derivatives, a plurality of processes for their preparation, and their use as herbicides, fungicides, antimycotics, insecticides and acaricides.

Pharmaceutical properties have previously been described in 3-acyl-pyrrolidine-2,4-diones (S. Suzuki and coworkers, Chem. Pharm. bull. 15 1120 (1967)). N-Phenyl-pyrrolidine-2,4-diones were furthermore synthesized by R. Schmierer and H. Mildenberger Liebigs Ann. Chem. 1985 1095. A biological activity of these compounds has not been described.

In EP-A 0,262,399 there are published compounds of a similar structure (3-aryl-pyrrolidine-2,4-diones), but nothing has been known of these compounds about a herbicidal, fungicidal, antimycotic, tickicidal, insecticidal or acaricidal activity.

New 3-aryl-pyrrolidine-2,4-dione (e) derivatives have now been found, which are represented by the formula (I)

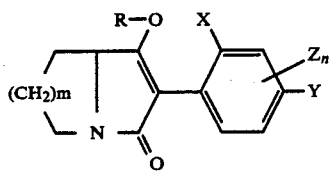

in which
X represents alkyl, halogen and alkoxy,
Y represents hydrogen, alkyl, halogen, alkoxy and halogenoalkyl,
Z represents alkyl, halogen and alkoxy,
m represents a number from 1-4,
n represents a number from 0-3,
R represents hydrogen or A, or represents the groups —CO—$R^1$, —CO—O—$R^2$ where
  A represents a metal cation equivalent or represents an ammonium ion,
  $R^1$ represents optionally halogen-substituted alkyl, alkenyl, alkoxyalkyl, alkylthioalkyl, polyalkoxyalkyl and optionally substituted cycloalkyl which can be interrupted by hetero atoms, or represents optionally substituted phenyl, optionally substituted phenoxyalkyl and substituted hetaryloxyalkyl and
  $R^2$ represents optionally halogen-substituted alkyl, cycloalkyl, alkenyl, alkoxyalkyl, polyalkoxyalkyl and optionally substituted phenyl,
as well as the pure enantiomeric forms of compounds of the formula (I).

The following sub-groups may be defined below:
(Ia): Compounds of the formula (I) where R=hydrogen,
(Ib): Compounds of the formula (I) where R=$COR^1$,
(Ic): Compounds of the formula (I) where R=$COOR^2$,
(Id): Compounds of the formula (I) where R=a metal ion equivalent or an ammonium ion.

Furthermore, it has been found that 3-aryl-pyrrolidine-2,4-diones or the enols thereof, of the formula (Ia)

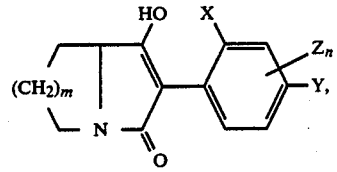

are obtained when (A) N-acylamino acid esters of the formula (II)

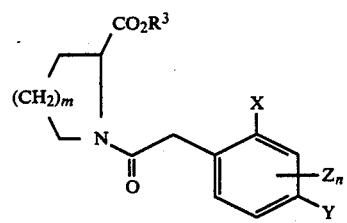

in which
X, Y, Z, m and n have the meanings mentioned herein, and
$R^3$ represents alkyl, preferably $C_1$-$C_6$-alkyl, are subjected to an intramolecular condensation reaction in the presence of a diluent and in the presence of a base.

(B) Furthermore, it has been found that compounds of the formula (Ib)

$$R^1-\overset{O}{\underset{\|}{C}}-O\quad \text{(Ib)}$$

are obtained when compounds of the formula (Ia)

(Ia)

in which
X, Y, Z, m and n have the abovementioned meanings, are reacted
(α) with acid halides of the general formula (III)

$$\text{Hal}-\overset{\|}{\underset{O}{C}}-R^1 \quad \text{(III)}$$

in which
$R^1$ has the abovementioned meaning and
Hal represents halogen, in particular chlorine and bromine,
if appropriate in the presence of a diluent and if appropriate in the presence of an acid-binding agent, or
(β) with carboxylic anhydrides of the general formula (IV)

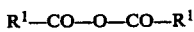 (IV)

in which
R¹ has the abovementioned meaning,
if appropriate in the presence of a diluent and if appropriate in the presence of an acid-binding agent.

(C) Furthermore, it has been found that compounds of the formula (Ic)

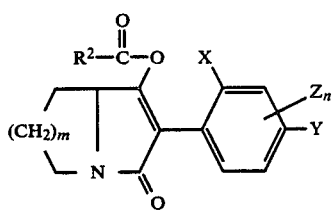 (Ic)

are obtained when compounds of the formula (Ia)

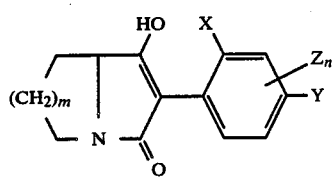 (Ia)

in which
X, Y, Z, m and n have the abovementioned meanings are reacted with chloroformic acid esters of the general formula (V)

 (V)

in which
R² has the abovementioned meaning,
if appropriate in the presence of a diluent and if appropriate in the presence of an acid-binding agent.

(D) Furthermore, it has been found that compounds of the formula (Id)

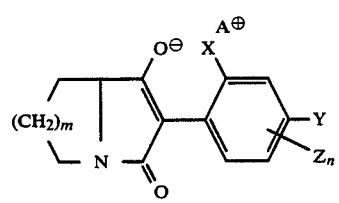 (Id)

in which
X, Y, Z, A, m and n have the abovementioned meanings are obtained when compounds of the formula (Ia)

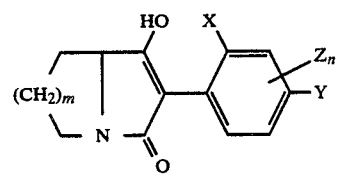 (Ia)

in which
X, Y, Z, m and n have the abovementioned meanings, are reacted with metal hydroxides or amines of the general formulae (VIII) and (IX)

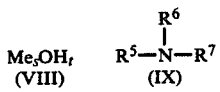

in which
Me represents monovalent or divalent metal ions,
s and t represent the number 1 and 2 and
R⁵, R⁶ and R⁷ independently of one another represent hydrogen and alkyl,
if appropriate in the presence of a diluent.

Surprisingly, it has been found that the new 3-aryl-pyrrolidine-2,4-diones of the formula (I) are distinguished by outstanding herbicidal, insecticidal, antimycotic and acaricidal effects.

Preferred compounds are condensed 1,5-alkylene-3-aryl-pyrrolidine-2,4-diones and the corresponding enol esters thereof, of the formula (I), in which
X represents $C_1$–$C_6$-alkyl, halogen and $C_1$–$C_6$-alkoxy,
Y represents hydrogen, $C_1$–$C_6$-alkyl, halogen, $C_1$–$C_6$-alkoxy and $C_1$–$C_3$-halogenoalkyl,
Z represents $C_1$–$C_6$-alkyl, halogen and $C_1$–$C_6$-alkoxy,
m represents a number from 1–4,
n represents a number from 0–3,
R represents hydrogen (Ia), or represents the groups of the formula

or

in which
A represents a metal cation equivalent or represents an ammonium ion,
R¹ represents optionally halogen-substituted: $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl and cycloalkyl which has 3–8 ring atoms and which can be interrupted by oxygen and/or sulphur,
or represents optionally halogen-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl;
or represents optionally halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl,
or represents optionally halogen- and $C_1$–$C_6$-alkyl-substituted phenoxy-$C_1$–$C_6$-alkyl,
or represents optionally halogen-, amino- and $C_1$–$C_6$-alkyl-substituted hetaryloxy-$C_1$–$C_6$-alkyl,
R² represents optionally halogen-substituted: $C_1$–$C_{20}$-alkyl, $C_2$–$C_{20}$-alkenyl, $C_1$–$C_8$-alkoxy-$C_2$–$C_8$-alkyl and $C_1$–$C_8$-polyalkoxy-$C_2$–$C_8$-alkyl,
or represents halogen-, nitro-, $C_1$–$C_6$-alkyl-, $C_1$–$C_6$-alkoxy-, $C_1$–$C_6$-halogenoalkyl-substituted phenyl,
and the enantiomerically pure forms of compounds of the formula (I).

Particularly preferred compounds of the formula (I) are those in which
X represents $C_1$–$C_4$-alkyl, halogen and $C_1$–$C_4$-alkoxy,
Y represents hydrogen, $C_1$–$C_6$-alkyl, halogen, $C_1$–$C_4$-alkoxy and $C_1$–$C_2$-halogenoalkyl,
Z represents $C_1$–$C_4$-alkyl, halogen and $C_1$–$C_4$-alkoxy,
m represents a number from 1–3,
n represents a number from 0–3, R represents hydrogen (Ia), or represents the groups of the formula —CO—R¹ (Ib), —CO—O—R² (Ic)

or

A (Id)

in which

A represents a metal cation equivalent or represents an ammonium ion,

R¹ represents optionally halogen-substituted: $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_2$–$C_6$-alkyl and cycloalkyl which has 3–7 ring atoms and which can be interrupted by 1–2 oxygen and/or sulphur atoms, or represents optionally halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, or represents optionally halogen-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents optionally halogen- and $C_1$–$C_6$-alkyl-substituted hetaryl, or represents optionally halogen- and $C_1$–$C_4$-alkyl-substituted phenoxy-$C_1$–$C_5$-alkyl, or represents optionally halogen-, amino- and $C_1$–$C_4$-alkyl-substituted hetaryloxy-$C_1$–$C_5$-alkyl, R² represents optionally halogen-substituted: $C_1$–$C_{16}$-alkyl, $C_2$–$C_{16}$-alkenyl, $C_1$–$C_{16}$-alkoxy-$C_2$–$C_6$-alkyl and $C_1$–$C_6$-polyalkoxy-$C_2$–$C_6$-alkyl, or represents halogen-, nitro-, $C_1$–$C_4$-alkyl-, $C_1$–$C_3$-alkoxy- or $C_1$–$C_3$-halogenoalkyl-substituted phenyl, and the enantiomerically pure forms of compounds of the formula (I).

Very particularly preferred compounds of the formula (I) are those in which

X represents methyl, ethyl, propyl, i-propyl, fluorine, chlorine, bromine, methoxy and ethoxy, Y represents hydrogen, methyl, ethyl, propyl, i-propyl, butyl, i-butyl, tert.-butyl, chlorine, bromine, methoxy, ethoxy and trifluoromethyl, Z represents methyl, ethyl, i-propyl, butyl, i-butyl, tert.-butyl, chlorine, bromine, methoxy and ethoxy, m represents a number from 1–2, n represents a number from 0–3, R represents hydrogen (Ia), or represents the groups of the formula —CO—R¹ (Ib), —CO—O—R² (Ic)

or

A (Id)

in which

A represents a metal cation equivalent or represents an ammonium ion,

R¹ represents optionally fluorine- or chlorine-substituted: $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxyl-$C_2$–$C_4$-alkyl and cycloalkyl which has 3–6 ring atoms and which can be interrupted by 1–2 oxygen and/or sulphur atoms, or represents optionally fluorine-, chlorine-, bromine-, methyl-, ethyl, propyl-, i-propyl-, methoxy-, ethoxy-, trifluoromethyl-, trifluoromethoxy- or nitro-substituted phenyl, or represents optionally fluorine-, chlorine-, bromine-, methyl-, ethyl-, propyl-, i-propyl-, methoxy-, ethoxy-, trifluoromethyl- or trifluoromethoxy-substituted phenyl-$C_1$–$C_3$-alkyl, or represents optionally fluorine-, chlorine-, bromine-, methyl- or ethyl-substituted pyridyl, pyrimidyl, thiazolyl and pyrazolyl, or represents optionally fluorine-, chlorine-, methyl- or ethyl-substituted phenoxy-$C_1$–$C_4$-alkyl, or represents optionally fluorine-, chlorine-, amino-, methyl- or ethyl-substituted pyridyloxy-$C_2$–$C_4$-alkyl, pyrimidyloxy-$C_1$–$C_4$-alkyl and thiazolyloxy-$C_1$–$C_4$-alkyl, R² represents optionally fluorine- or chlorine-substituted: $C_1$–$C_{14}$-alkyl, $C_2$–$C_{14}$-alkenyl, $C_1$–$C_4$-alkoxy-$C_2$–$C_6$-alkyl and $C_1$–$C_4$-polyalkoxy-$C_2$–$C_6$-alkyl, or represents optionally fluorine-, chlorine-, nitro-, methyl-, ethyl-, propyl-, i-propyl-, methoxy-, ethoxy- or trifluoromethyl-substituted phenyl, as well as the enantiomerically pure forms of compounds of the formula I.

If, according to process (A), ethyl N-(2,6-dichlorophenylacetyl)-piperidine-2-carboxylate is used, the course of the process according to the invention can be represented by the following equation:

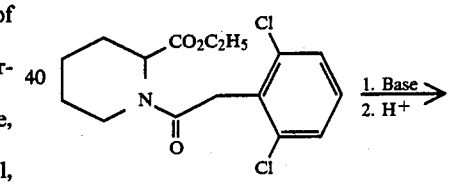

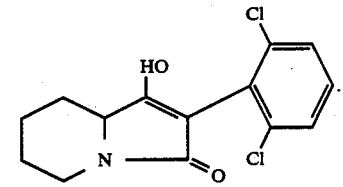

If, according to process (B) (variant α), 3-(2,4,6-trimethylphenyl)-1,5-trimethylene-pyrrolidine-2,4-dione and pivaloyl chloride are used as starting substance, the course of the process according to the invention can be represented by the following equation:

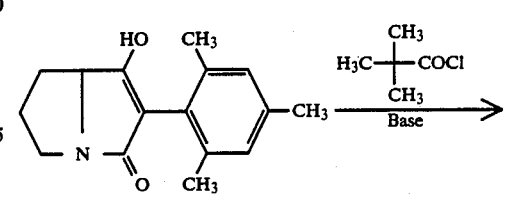

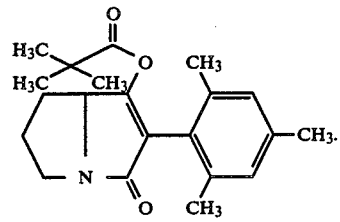

If, according to process B (variant β), 3-(2,4,5-trimethylphenyl)-1,5-tetramethylene-pyrrolidine-2,4-dione and acetic acid are used, the course of the process according to the invention can be represented by the following equation.

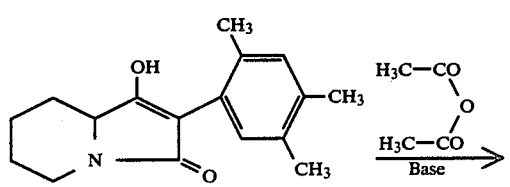

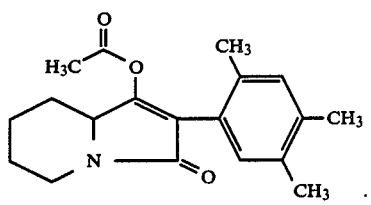

If, according to process (C), 3-(2,4-dichlorophenyl)-1,5-tetramethylene-pyrrolidine-2,4-dione and ethoxyethyl chloroformate are used, the course of the process according to the invention can be represented by the following equation.

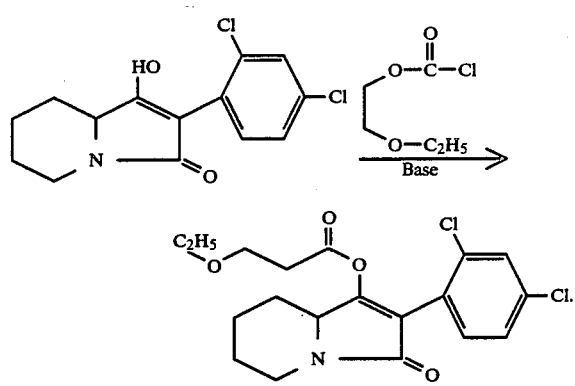

If, according to process (D), 3-(2,4,6-trimethylphenyl)-1,5-trimethylene-pyrrolidine-2,4-dione and NaOH are used, the course of the process according to the invention can be represented by the following equation:

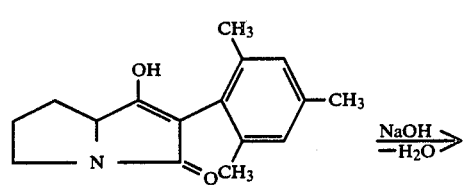

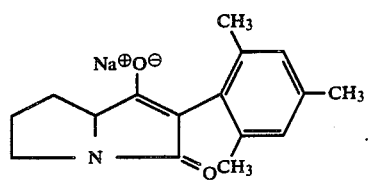

The compounds required as starting substances in the above process (A), of the formula (II)

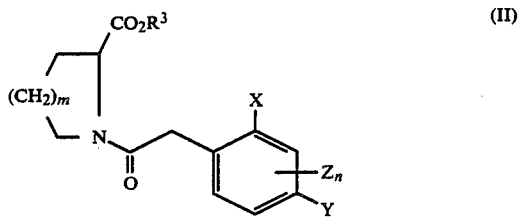

(II)

in which

X, Y, Z, m, n and $R^3$ have the abovementioned meanings, were hitherto unknown, but can be prepared in a simple manner by methods which are known in principle. Thus, for example, acyl-amino acid esters of the formula (II) are obtained when (a) amino acid esters of the formula (VI)

(VI)

in which $R^3$ represents alkyl and m represents the number 1 or 2 are acylated with phenylacetic acid halides of the formula (VII)

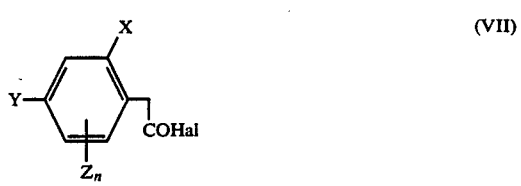

(VII)

in which

X, Y, Z and n have the abovementioned meaning and Hal represents chlorine or bromine, (general methodology described in: Chem. Reviews 52 237–416 (1953));

or when (b) acylamino acids of the formula (IIa),

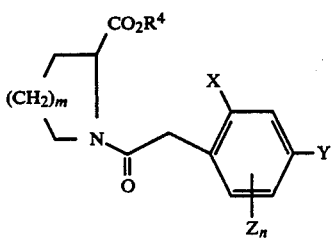

in which
X, Y, Z, m and n have the abovementioned meanings and
R⁴ represents hydrogen,
are esterified (general methodology described in: Chem. Ind. (London) 1568 (1968)).

For example, compounds of the formula (IIa) can be obtained from the phenylacetic acid halides of the formula (VII) and amino acids of the formula (VIa)

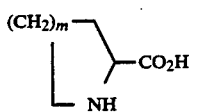

ps in which
m represents the number 1 or 2,
by the method of Schotten-Baumann (Organikum [Laboratory Practical of Organic Chemistry] 9th edition 446 (1970) VEB Deutscher Verlag der Wissenschaften, Berlin).

The following compounds of the formula (II) may be mentioned by way of example:
(1) Ethyl N-(2,4-dichlorophenylacetyl)-piperidine-2-carboxylate
(2) Ethyl N-(2-fluoro-4-chlorophenylacetyl)-piperidine-2-carboxylate
(3) Ethyl N-(2,6-dichlorophenylacetyl)-piperidine-2-carboxylate
(4) Ethyl N-(2-fluoro-6-chlorophenylacetyl)-piperidine-2-carboxylate
(5) Ethyl N-(2,4,6-trimethylphenylacetyl)-piperidine-2-carboxylate
(6) Ethyl N-(2-fluoro-6-chloro-4-trifluoromethyl-phenylacetyl)-piperidine-2-carboxylate
(7) Ethyl N-(2,6-dichloro-4-trifluoromethyl-phenylacetyl)-piperidine-2-carboxylate
(8) Ethyl N-(2,4,5-trimethyl-phenylacetyl)-piperidine-2-carboxylate
(9) Ethyl N-(2-fluoro-5-chloro-4-trifluoromethyl-phenylacetyl)-piperidine-2-carboxylate
(10) Ethyl N-(2,4,6-triisopropyl-phenylacetyl)-piperidine-2-carboxylate
(11) Ethyl N-(2,4,6-trichlorophenylacetyl)-piperidine-2-carboxylate
(12) Ethyl N-(2-chloro-3-methyl-phenylacetyl)-piperidine-2-carboxylate
(13) Ethyl N-(3-bromo-2,4,6-trimethyl-phenylacetyl)-piperidine-2-carboxylate
(14) Ethyl N-pentamethyl-phenylacetyl)-piperidine-2-carboxylate
(15) Ethyl N-(4-tert.-butyl-2-methyl-phenylacetyl)-piperidine-2-carboxylate
(16) Ethyl N-(4-tert.-butyl-2,6-dimethyl-phenylacetyl)-piperidine-2-carboxylate
(17) Ethyl N-(2,3,4,6-tetramethyl-phenylacetyl)-piperidine-2-carboxylate
(18) Ethyl N-(2,3,6-trichloro-phenylacetyl)-piperidine-2-carboxylate
(19) Ethyl N-(2,4-dimethyl-phenylacetyl)-piperidine-2-carboxylate
(20) Ethyl N-(2,3,4,5-tetramethyl-phenylacetyl)-piperidine-2-carboxylate
(21) Ethyl N-(2,3,5,6-tetramethyl-phenylacetyl)-piperidine-2-carboxylate
(22) Ethyl N-(2-fluoro-4,6-dimethyl-phenylacetyl)-piperidine-2-carboxylate
(23) Ethyl N-(4-fluoro-2,6-dimethyl-phenylacetyl)-piperidine-2-carboxylate
(24) Methyl N-(2,4-dichloro-phenylacetyl)-pyrrolidine-2-carboxylate
(25) Methyl N-(2,6-dichloro-phenylacetyl)-pyrrolidine-2-carboxylate
(26) Methyl N-(2,4,6-trimethyl-phenylacetyl)-pyrrolidine-2-carboxylate
(27) Methyl N-(2,4,5-trimethyl-phenylacetyl)-pyrrolidine-2-carboxylate
(28) Methyl N-(2-fluoro-6-chloro-phenylacetyl)-pyrrolidine-2-carboxylate
(29) Methyl N-(2,6-dichloro-4-trifluoromethyl-phenylacetyl)-pyrrolidine-2-carboxylate
(30) Methyl N-(2,4,6-trichloro-phenylacetyl)-pyrrolidine-2-carboxylate
(31) Methyl N-(2,3,6-trichloro-phenylacetyl)-pyrrolidine-2-carboxylate
(32) Methyl N-(2-fluoro-4,6-dimethyl-phenylacetyl)-pyrrolidine-2-carboxylate
(33) Methyl N-(4-fluoro-2,6-dimethyl-phenylacetyl)-pyrrolidine-2-carboxylate The following compounds of the formula (IIa) may be mentioned by way of example:
(34) N-2,4-Dichlorophenylacetyl-prolinee
(35) N-2-Fluoro-6-chlorophenylacetyl-prolinee
(36) N-2,6-Dichlorophenylacetyl-prolinee
(37) N-2,4,6-Trimethylphenylacetyl-prolinee
(38) N-2,4,5-trimethylphenylacetyl-prolinee
(39) N-2,6-Dichloro-4-trifluoromethyl-phenylacetyl-prolinee When carrying out process (A) according to the invention, the reaction temperatures can be varied within a relatively wide range. In general, the process is carried out at temperatures between 0° C. and 250° C., preferably between 50° C. and 150° C.

Process (A) according to the invention is generally carried out under atmospheric pressure.

When carrying out process (A) according to the invention, the reactants of the formulae (II) and the deprotonating bases are generally employed in approximately equimolar amounts. However, it is also possible to use one or the other component in a relatively large excess (up to 3 moles).

Process (A) is characterized in that compounds of the formula (II) in which X, Y, Z, m, n and R³ have the abovementioned meanings are subjected to intramolecular condensation in the presence of bases.

Diluents which can be employed in process (A) according to the invention are all customary inert organic solvents. Hydrocarbons, such as cyclohexane, toluene and xylene, furthermore ethers, such as dibutyl ether, tetrahydrofuran, dioxane, glycol dimethyl ether and diglycol dimethyl ether, and moreover polar solvents, such as dimethyl sulphoxide, sulpholane, dimethylformamide and N-methyl-pyrrolidone, can preferably be used.

Deprotonating agents which can be employed in carrying out process (A) according to the invention are all customary proton acceptors. The oxides, hydroxides and carbonates of alkali metals and alkaline earth metals, such as sodium hydroxide, potassium hydroxide, magnesium oxide, calcium oxide, sodium carbonate, potassium carbonate and calcium carbonate, which can also be employed in the presence of phase transfer catalysts, such as, for example, triethylbenzylammonium chloride, tetrabutylammonium bromide, Adogen 464 or TDA 1, can preferably by used. Amides and hydrides of alkali metals and alkaline earth metals, such as sodium amide, sodium hydride and calcium hydride, and, moreover, also alkali metal alkoxides, such as sodium methoxide, sodium methoxide and potassium tert.-butoxide, can furthermore be employed.

Adogen 464=Methyltrialkyl($C_8$-$C_{10}$)ammonium chloride
TDA 1=Tris-(methoxyethoxyethyl)-amine Process (Bα) is characterized in that compounds of the formula (Ia) are reacted with carboxylic acid halides of the formula (III).

When the acid halides are used, diluents which can be employed in process (Bα) according to the invention are all solvents which are inert towards these compounds. Hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, and in addition carboxylic acid esters, such as ethyl acetate, and also strongly polar solvents, such as dimethyl sulphoxide and sulpholane, can preferably be used. If the stability of the acid halide to hydrolysis permits, the reaction can also be carried out in the presence of water.

Suitable acid-binding agents for the reaction of process (Bα) according to the invention are all customary acid acceptors if the corresponding carboxylic acid halides are used. Tertiary amines, such as triethylamine, pyridine, DABCO, DBU, DBA, Hünig bas and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, can preferably be used.

When carrying out process (Bα) according to the invention, the reaction temperatures can also be varied within a relatively wide range, even when carboxylic acid halides are used. In general, the process is carried out at temperatures between −20° C. and +150° C., preferably between 0° C. and 100° C.

When carrying out process (Bα) according to the invention, the starting substances of the formula (Ia) and the carboxylic acid halide of the formula (III) are generally used in approximately equimolar amounts. However, it is also possible to employ the carboxylic acid anhydride in a relatively large excess (up to 5 moles). Working-up is carried out by customary methods.

Process (Bβ) is characterized in that compounds of the formula (Ia) are reacted with carboxylic acid hydrides of the formula (IV).

If in process (Bβ) according to the invention carboxylic anhydride is used as the reactant for the formula (IV), it is possible to use as diluents preferably those diluents which are also preferably suitable when acid halides are used. Alternatively, carboxylic acid hydride which is employed in excess can also act simultaneously as the diluent.

In process (Bα), according to the invention, the reaction temperatures can also be varied within a relatively wide range even when carboxylic anhydrides are used. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a relatively large excess (up to 5 moles). Working-up is carried out by customary methods.

In general, a procedure is followed in which the diluent and the carboxylic anhydride, which is present in excess, as well as the carboxylic acid which forms, are removed by distillation or by washing with an organic solvent or using water.

Process (C) is characterized in that compounds of the formula (Ia) are reacted with chloroformic acid esters of the formula (V).

If the corresponding chloroformic acid esters are used, suitable acid-binding agents in the reaction of process (C) according to the invention are all customary acid acceptors. Tertiary amines, such as triethylamine, pyridine, DABCO, DBC, DBA, Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, can preferably be used.

When the chloroformic acid esters are used, diluents which can be employed in process (C) according to the invention are all solvents which are inert towards these compounds. Hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, and in addition carboxylic acid esters, such as ethyl acetate, and also strongly polar solvents, such as dimethyl sulphoxide and sulpholane, can preferably be used.

When carrying out process (C) according to the invention, the reaction temperatures can be varied within a relatively wide range when the chloroformic acid esters are used as the carboxylic acid derivatives of the formula (V). If the process is carried out in the presence of a diluent and of an acid-binding agent, the reaction temperatures generally are between −20° C. and +100° C., preferably between 0° C. and 50° C.

Process (C) according to the invention is generally carried out under atmospheric pressure.

When carrying out process (C) according to the invention, the starting substances of the formula (Ia) and the corresponding chloroformic acid ester of the formula (V) are generally used in approximately equivalent amounts. However, it is also possible to employ one or the other component in a relatively large excess (up to 2 moles). Working-up is then carried out by customary methods. In general, a procedure is followed in which the precipitated salts are removed and the reaction mixture which remains is concentrated by stripping off the solvent.

Process (D) is characterized in that compounds of the formula (Ia) are reacted with acetal hydroxides (VIII) or amines (IX).

Diluents which can be employed in the process according to the invention are preferably ethers, such as tetrahydrofuran, dioxane or diethyl ether, and also alcohols, such as methanol, ethanol or isopropanol, and also water. Process (D) according to the invention is generally carried out under atmospheric pressure. The reaction temperatures are generally between −20° C. and 100° C., preferably between 0° C. and 50° C.

When carrying out process (D) according to the invention, the starting substances of the formula (Ia) or (IX) are generally used in approximately equimolar amounts. However, it is also possible to employ one or the other component in a relatively large excess (up to 2 moles). In general, a procedure is followed in which the reaction mixture is concentrated by stripping off the diluent.

EXAMPLE 1

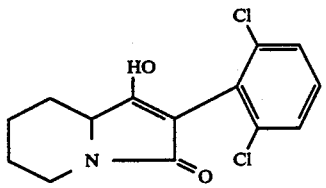

8.4 g (0.28 mol) of sodium hydride (80% strength) are introduced into 150 ml of absolute toluene. After 80 g (0.23 mol) of ethyl N-(2,6-dichlorophenylacetyl)-piperidine-2-carboxylate in 400 ml of absolute toluene have been added dropwise, the mixture is refluxed for 6 hours. 30 ml of ethanol are added dropwise while cooling in an ice bath, the batch is evaporated in vacuo on a rotary evaporator, the residue is dissolved in 1 N NaOH, and 3-(2,6-dichlorophenyl)-1,5-tetramethylene-pyrrolidine-2,4-dione is precipitated at 0°-20° C. using concentrated HCl. For purification, the product is boiled with chloroform, n-hexane is then added, and the colourless product which has precipitated is filtered off with suction.

Yield: 40.5 g (59.1% of theory) M.p. >250° C.

EXAMPLE 2

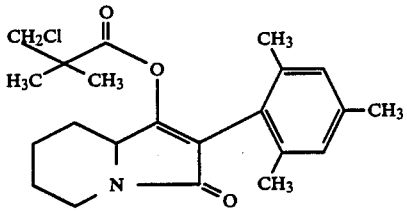

4.6 g (15 mmol) of 3-(2,4,6-trimethylphenyl)-1,5-tetramethylene-pyrrolidine-2,4-dione are suspended in 50 ml of absolute THF, and the mixture is treated with 1.22 ml (15 mmol) of absolute pyridine and 2.54 ml (15 mmol) of ethyl-diisopropylamine. 1.94 ml (15 mmol) of 3-chloro-pivaloyl chloride, dissolved in 5 ml of absolute THF, are added dropwise at 0°-10° C. to this mixture, followed by stirring for 30 minutes. The precipitate is filtered off, the solution is evaporated in vacuo on a rotary evaporator, and the residue is chromatographed on silica gel using cyclohexane/ethyl acetate 1:1.

Crystallization from ether/n-hexane gives 3.93 g (70% of theory) of 4-(3-chloropivaloyloxy)-3-(2,4,6-trimethylphenyl)-1,5-tetramethylene-3-pyrrolin-2-one of melting point 102° C.

EXAMPLE 3

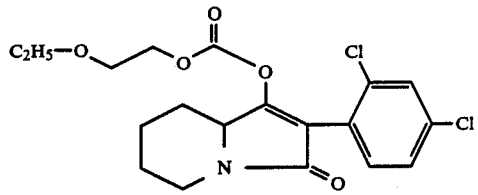

4.47 g (15 mmol) of 3-(2,4-dichlorophenyl)1,5-tetramethylenepyrrrolidine-2,4-dione in 50 ml of absolute THF are treated with 1.22 ml (15 mmol) of absolute pyridine. 2.44 g (15 mmol) of ethoxyethyl chloroformate, dissolved in 5 ml of absolute THF, are added dropwise at 0°-10° C., followed by stirring for 30 minutes. After the precipitate has been filtered off, the filtrate is evaporated in vacuo on a rotary evaporator, and the residue is chromatographed on silica gel using cyclohexane/ethyl acetate 1:2 and crystallized from ether/n-hexane.

Yield: 5.2 g (83.7% of theory) of 4-ethoxyethyloxycarbonyloxy-3-(2,4-dichlorophenyl)-1,5-tetramethylene-3-pyrrolin-2-one of melting point 80° C.

The 3-aryl-pyrrolidin-2,4-dione (e) derivatives of the formula (Ia)–(Ic), which are listed by their formulae in Tables 1–3 below, are obtained in a manner corresponding to the Preparation Examples and following the general preparation instructions.

TABLE 1

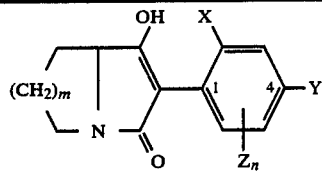

(Ia)

| Example No. | X | Y | $Z_n$ | m | M.P. °C. |
|---|---|---|---|---|---|
| 4 | Cl | Cl | — | 1 | >218 |
| 5 | Cl | H | 6-Cl | 1 | >230 |
| 6 | CH₃ | CH₃ | 5-CH₃ | 1 | 228 |
| 7 | CH₃ | CH₃ | 6-CH₃ | 1 | >230 |
| 8 | Cl | H | — | 2 | 174 |
| 9 | F | Cl | — | 2 | 207 |
| 10 | Cl | Cl | — | 2 | 208 |
| 11 | Cl | H | 6-F | 2 | 230 |
| 12 | CH₃ | CH₃ | 5-CH₃ | 2 | 210 |
| 13 | CH₃ | CH₃ | 6-CH₃ | 2 | >230 |
| 14 | F | CF₃ | 5-F | 2 | 228 |
| 15 | F | CF₃ | 5-Cl | 2 | >230 |
| 16 | F | CF₃ | 6-Cl | 2 | 227 |
| 17 | Cl | CF₃ | 6-Cl | 2 | >230 |
| 18 | CH₃ | H | 6-CH₃ | 2 | |
| 19 | CH₃ | H | 6-Cl | 2 | |
| 20 | CH₃ | CH₃ | 3-CH₃ | 2 | |
| 21 | CH₃ | CH₃ | 3.5-di-CH₃ | 2 | 160 |
| 22 | CH₃ | CH₃ | 3.5.6-tri-CH₃ | 2 | >230 |
| 23 | CH₃ | t-C₄H₉ | 6-CH₃ | 2 | >230 |
| 24 | CH₃ | F | — | 2 | 191 |
| 25 | CH₃ | CH₃ | — | 2 | 192 |
| 26 | CH₃ | t-C₄H₉ | — | 2 | 210 |
| 27 | Cl | H | 3-CH₃ | 2 | 195 |
| 28 | Cl | H | 3.5-di-Cl | 2 | >230 |

TABLE 1-continued

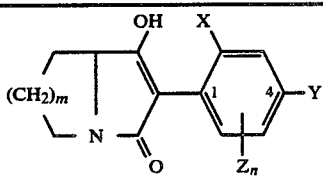
(Ia)

| Example No. | X | Y | $Z_n$ | m | M.P. °C. |
|---|---|---|---|---|---|
| 29 | Cl | Cl | 6-Cl | 2 | >230 |
| 30 | $CH_3$ | F | 6-$CH_3$ | 2 | >230 |
| 31 | $CH_3$ | $CH_3$ | 6-F | 2 | 207 |
| 32 | i-$C_3H_7$ | i-$C_3H_7$ | 6-i-$C_3H_7$ | 2 | >230 |
| 33 | $CH_3$ | H | 3.5.6-tri-$CH_3$ | 2 | >230 |
| 34 | $CH_3$ | $CH_3$ | 3.6-di-$CH_3$ | 2 | >230 |
| 35 | $CH_3$ | $CH_3$ | 3-Br-6-$CH_3$ | 2 | >230 |

TABLE 2

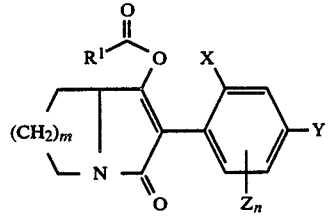
(Ib)

| Example No. | X | Y | $Z_n$ | m | $R^1$ | m.p. °C. |
|---|---|---|---|---|---|---|
| 36 | Cl | Cl | — | 1 | $CH_3-$ | 95 |
| 37 | Cl | Cl | — | 1 | $(CH_3)_2CH-$ | Oil |
| 38 | Cl | Cl | — | 1 | $(CH_3)_3C-$ | Oil |
| 39 | Cl | Cl | — | 1 | $(CH_3)_2-CH-C(CH_3)_2-$ | Oil |
| 40 | Cl | H | 6-Cl | 1 | $CH_3-$ | 80 |
| 41 | Cl | H | 6-Cl | 1 | $(CH_3)_2CH-$ | Oil |
| 42 | Cl | H | 6-Cl | 1 | $(CH_3)_3C-$ | 102 |
| 43 | Cl | H | 6-Cl | 1 | $(CH_3)_2-CH-C(CH_3)_2-$ | Oil |
| 44 | Cl | H | 6-Cl | 1 | $(CH_3)_3C-CH_2-$ | Oil |
| 45 | Cl | H | 6-Cl | 1 | $(CH_3)_2C=CH-$ | Oil |
| 46 | Cl | H | 6-Cl | 1 | 2-Cl-phenyl | 85 |
| 47 | Cl | H | 6-Cl | 1 | 3-Cl-phenyl | 98 |
| 48 | Cl | H | 6-Cl | 1 | 4-Cl-phenyl | 143 |
| 49 | $CH_3$ | $CH_3$ | 5-$CH_3$ | 1 | $CH_3$ | Oil |
| 50 | $CH_3$ | $CH_3$ | 5-$CH_3$ | 1 | $(CH_3)_2CH-$ | Oil |
| 51 | $CH_3$ | $CH_3$ | 5-$CH_3$ | 1 | $(CH_3)_3C-$ | Oil |
| 52 | $CH_3$ | $CH_3$ | 5-$CH_3$ | 1 | $(CH_3)_2CHC(CH_3)_2-$ | Oil |
| 53 | $CH_3$ | $CH_3$ | 6-$CH_3$ | 1 | $CH_3$ | Oil |
| 54 | $CH_3$ | $CH_3$ | 6-$CH_3$ | 1 | $(CH_3)_2CH-$ | Oil |
| 55 | $CH_3$ | $CH_3$ | 6-$CH_3$ | 1 | $(CH_3)_3C-$ | Oil |
| 56 | $CH_3$ | $CH_3$ | 6-$CH_3$ | 1 | $(CH_3)_2CH-(CH_3)_2-C-$ | Oil |
| 57 | $CH_3$ | $CH_3$ | 6-$CH_3$ | 1 | $C_4H_9-CH(C_2H_5)-$ | Oil |
| 58 | $CH_3$ | $CH_3$ | 6-$CH_3$ | 1 | $(CH_3)_3C-CH_2-$ | Oil |
| 59 | $CH_3$ | $CH_3$ | 6-$CH_3$ | 1 | $CH_2=CH(CH_2)_7-$ | Oil |
| 60 | $CH_3$ | $CH_3$ | 6-$CH_3$ | 1 | $(CH_3)_2-CH-CH_2-$ | Oil |
| 61 | $CH_3$ | $CH_3$ | 6-$CH_3$ | 1 | $C_2H_5-C(CH_3)(CH_3)-$ | Oil |
| 62 | $CH_3$ | $CH_3$ | 6-$CH_3$ | 1 | $Cl-C(CH_3)_2-CH_3$ | Oil |

TABLE 2-continued

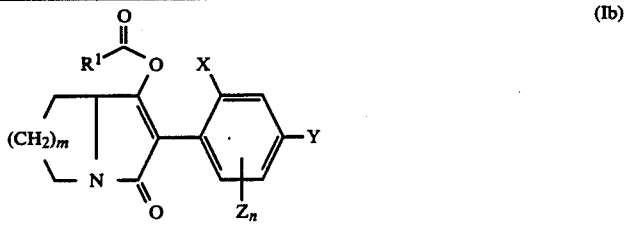
(Ib)

| Example No. | X | Y | $Z_n$ | m | $R^1$ | m.p. °C. |
|---|---|---|---|---|---|---|
| 63 | CH₃ | CH₃ | 6-CH₃ | 1 | Cl₂C(CH₃)– | 105 |
| 64 | CH₃ | CH₃ | 6-CH₃ | 1 | H₃C–O–CH₂–C(CH₃)₂– | Oil |
| 65 | CH₃ | CH₃ | 6-CH₃ | 1 | H₃C–O–CH₂–C(CH₃)(OCH₃)– | Oil |
| 66 | CH₃ | CH₃ | 6-CH₃ | 1 | F₂C(CH₃)– | Oil |
| 67 | CH₃ | CH₃ | 6-CH₃ | 1 | (H₃C)₂C=CH– | Oil |
| 68 | CH₃ | CH₃ | 6-CH₃ | 1 | H₃C–S–CH₂– | 105 |
| 69 | CH₃ | CH₃ | 6-CH₃ | 1 | C₂H₅–O–C(CH₃)₂– | Oil |
| 70 | CH₃ | CH₃ | 6-CH₃ | 1 | H₃C–O–(CH₂)₂–O–C(CH₃)₂– | Oil |
| 71 | CH₃ | CH₃ | 6-CH₃ | 1 | 2-methyl-1,3-dioxan-2-yl | 120 |
| 72 | CH₃ | CH₃ | 6-CH₃ | 1 | 2-ethyl-1,3-dioxan-2-yl | Oil |
| 73 | CH₃ | CH₃ | 6-CH₃ | 1 | 2-NO₂–C₆H₄– | 115 |
| 74 | CH₃ | CH₃ | 6-CH₃ | 1 | 3-NO₂–C₆H₄– | 106 |
| 75 | CH₃ | CH₃ | 6-CH₃ | 1 | 4-NO₂–C₆H₄– | 120 |

TABLE 2-continued
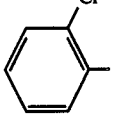
(Ib)
| Example No. | X | Y | $Z_n$ | m | $R^1$ | m.p. °C. |
|---|---|---|---|---|---|---|
| 76 | $CH_3$ | $CH_3$ | 6-$CH_3$ | 1 | 2-Cl-phenyl | oil |
| 77 | $CH_3$ | $CH_3$ | 6-$CH_3$ | 1 | 3-Cl-phenyl | Oil |
| 78 | $CH_3$ | $CH_3$ | 6-$CH_3$ | 1 | 4-Cl-phenyl | 73 |
| 79 | $CH_3$ | $CH_3$ | 6-$CH_3$ | 1 | 2-$CH_3$-phenyl | 118 |
| 80 | $CH_3$ | $CH_3$ | 6-$CH_3$ | 1 | 3-$CH_3$-phenyl | 108 |
| 81 | $CH_3$ | $CH_3$ | 6-$CH_3$ | 1 | 4-$CH_3$-phenyl | Oil |
| 82 | $CH_3$ | $CH_3$ | 6-$CH_3$ | 1 | 2-$OCH_3$-phenyl | 122 |
| 83 | $CH_3$ | $CH_3$ | 6-$CH_3$ | 1 | 3-$OCH_3$-phenyl | 102 |
| 84 | $CH_3$ | $CH_3$ | 6-$CH_3$ | 1 | 4-$OCH_3$-phenyl | Oil |
| 85 | Cl | Cl | — | 2 | $CH_3$— | 120 |
| 86 | Cl | Cl | — | 2 | $(CH_3)_2CH$— | 68 |
| 87 | Cl | Cl | — | 2 | $(CH_3)_3C$— | 94 |
| 88 | Cl | Cl | — | 2 | $(CH_3)_2CH$—$C(CH_3)_2$— | 62 |

TABLE 2-continued

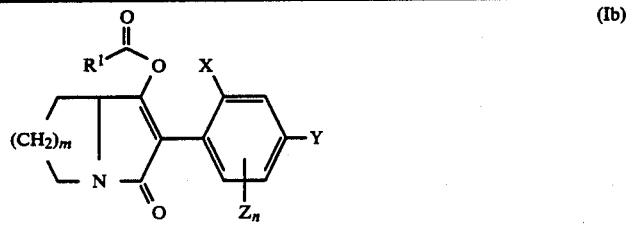
(Ib)

| Example No. | X | Y | $Z_n$ | m | $R^1$ | m.p. °C. |
|---|---|---|---|---|---|---|
| 89 | Cl | Cl | — | 2 | (CH₃)₂C(CH₃)CH₂Cl (neopentyl-Cl: H₃C-C(CH₃)(CH₃)-CH₂Cl) | Oil |
| 90 | Cl | Cl | — | 2 | (CH₃)₂C(CH₃)CH₂-CH₂Cl | 125 |
| 91 | Cl | H | 6-Cl | 2 | $CH_3-$ | 120 |
| 92 | Cl | H | 6-Cl | 2 | $(CH_3)_2CH-$ | 82 |
| 93 | Cl | H | 6-Cl | 2 | $(CH_3)_3C-$ | 110 |
| 94 | Cl | H | 6-Cl | 2 | $(CH_3)_2CH-C(CH_3)_2-$ | 92 |
| 95 | Cl | H | 6-Cl | 2 | $CH_3-S-CH_2-$ | 126 |
| 96 | Cl | H | 6-Cl | 2 | 1,3-dioxane-2-yl-CH₃ (2-methyl-1,3-dioxan-2-yl) | 150 |
| 97 | Cl | H | 6-Cl | 2 | 4-Cl-C₆H₄- | 150 |
| 98 | Cl | H | 6-Cl | 2 | $H_3C-O-CH_2CH_2-O-CH_2-C(CH_3)_2-$ | 106 |
| 99 | Cl | H | 6-Cl | 2 | 2-ethyl-1,3-dioxan-2-yl | 162 |
| 100 | Cl | H | 6-Cl | 2 | $H_3C-O-CH_2-C(CH_3)_2-$ | 130 |
| 101 | Cl | H | 6-Cl | 2 | $C_2H_5O-CH_2-C(CH_3)_2-$ | 107 |
| 102 | Cl | H | 6-Cl | 2 | $(H_3C-O-CH_2)_2C(CH_3)-$ | 107 |
| 103 | Cl | H | 6-Cl | 2 | $(H_3C-O-CH_2)_3C-$ | 105 |
| 104 | Cl | H | 6-Cl | 2 | $(ClCH_2)_2C(CH_3)-$ | 126 |
| 105 | Cl | H | 6-Cl | 2 | $(FCH_2)_2C(CH_3)-$ | 114 |
| 106 | Cl | H | 6-Cl | 2 | $H_5C_2-O-CH_2CH_2-$ | Oil |

TABLE 2-continued

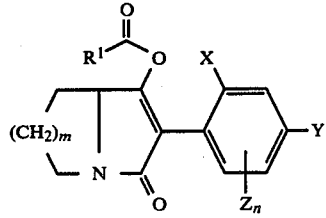
(Ib)

| Example No. | X | Y | $Z_n$ | m | $R^1$ | m.p. °C. |
|---|---|---|---|---|---|---|
| 107 | Cl | H | 6-Cl | 2 | 1-methylcyclohexyl | 136 |
| 108 | Cl | H | 6-Cl | 2 | (CH₃)₂C=C(CH₃)— | Oil |
| 109 | Cl | H | 6-Cl | 2 | (CH₃)₃C—CH₂— | Oil |
| 110 | Cl | H | 6-Cl | 2 | 4-Cl-C₆H₄-CH(C₂H₅)— | 122 |
| 111 | Cl | H | 6-Cl | 2 | CH₂=CH(CH₂)₇— | Oil |
| 112 | Cl | H | 6-Cl | 2 | (2-CH₃-4-Cl-phenoxybutyl) | Oil |
| 113 | Cl | H | 6-Cl | 2 | (4-amino-3,5-dichloro-6-fluoro-2-ethoxypyridinyl) | |
| 114 | Cl | H | 6-F | 2 | CH₃— | Oil |
| 115 | Cl | H | 6-F | 2 | (CH₃)₃C— | 102 |
| 116 | CH₃ | CH₃ | — | 2 | CH₃— | Oil |
| 117 | CH₃ | CH₃ | — | 2 | (CH₃)₂CH— | Oil |
| 118 | CH₃ | CH₃ | — | 2 | (CH₃)₃C— | 65 |
| 119 | CH₃ | CH₃ | — | 2 | (CH₃)₂CH—(CH₃)₂C— | Oil |
| 120 | CH₃ | t-C₄H₉ | — | 2 | CH₃— | Oil |
| 121 | CH₃ | t-C₄H₉ | — | 2 | (CH₃)₂CH— | Oil |
| 122 | CH₃ | t-C₄H₉ | — | 2 | (CH₃)₃C— | Oil |
| 123 | CH₃ | CH₃ | 5-CH₃ | 2 | CH₃ | 102 |
| 124 | CH₃ | CH₃ | 5-CH₃ | 2 | (CH₃)₂CH— | 88 |
| 125 | CH₃ | CH₃ | 5-CH₃ | 2 | (CH₃)₃C— | 103 |
| 126 | CH₃ | CH₃ | 5-CH₃ | 2 | (CH₃)₂CH—(CH₃)₂C— | Oil |
| 127 | CH₃ | CH₃ | 5-CH₃ | 2 | C₄H₉CH(C₂H₅)— | |
| 128 | CH₃ | CH₃ | 6-CH₃ | 2 | CH₃— | Oil |
| 129 | CH₃ | CH₃ | 6-CH₃ | 2 | (CH₃)₂CH— | Oil |
| 130 | CH₃ | CH₃ | 6-CH₃ | 2 | (CH₃)₃C— | 93 |
| 131 | CH₃ | CH₃ | 6-CH₃ | 2 | (CH₃)₂CH—(CH₃)₂C— | 68 |
| 132 | CH₃ | CH₃ | 6-CH₃ | 2 | C₄H₉—CH(C₂H₅)— | Oil |
| 133 | CH₃ | CH₃ | 6-CH₃ | 2 | CH₃S—CH₂— | 93 |
| 134 | CH₃ | CH₃ | 6-CH₃ | 2 | C₂H₅—O—CH₂— | Oil |

TABLE 2-continued

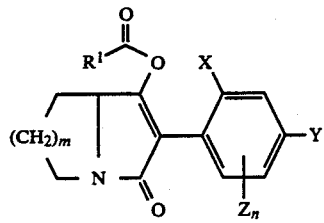
(Ib)

| Example No. | X | Y | $Z_n$ | m | $R^1$ | m.p. °C. |
|---|---|---|---|---|---|---|
| 135 | $CH_3$ | $CH_3$ | 6-$CH_3$ | 2 | (1,3-dioxane-2-yl)-C($CH_3$)- | 100 |
| 137 | $CH_3$ | $CH_3$ | 6-$CH_3$ | 2 | $H_3C-O-CH_2CH_2-O-CH_2-C(CH_3)_2$- | Oil |
| 138 | $CH_3$ | $CH_3$ | 6-$CH_3$ | 2 | (1,3-dioxane-2-yl)-C($C_2H_5$)- | 100 |
| 139 | $CH_3$ | $CH_3$ | 6-$CH_3$ | 2 | $H_3C-O-CH_2-C(CH_3)_2$- | 52 |
| 139 | $CH_3$ | $CH_3$ | 6-$CH_3$ | 2 | $H_5C_2O-CH_2-C(CH_3)_2$- | 71 |
| 140 | $CH_3$ | $CH_3$ | 6-$CH_3$ | 2 | $(H_3C-O-CH_2)_2C(CH_3)$- | Oil |
| 141 | $CH_3$ | $CH_3$ | 6-$CH_3$ | 2 | $(H_3C-O-CH_2)_3C-$ | 108 |
| 142 | $CH_3$ | $CH_3$ | 6-$CH_3$ | 2 | $(ClCH_2)_2C(CH_3)$- | 112 |
| 143 | $CH_3$ | $CH_3$ | 6-$CH_3$ | 2 | $(FCH_2)_2C(CH_3)$- | 83 |
| 144 | $CH_3$ | $CH_3$ | 6-$CH_3$ | 2 | 1-methylcyclohexyl | 103 |
| 145 | $CH_3$ | $CH_3$ | 6-$CH_3$ | 2 | 2,4-dichloro-1-ethoxyphenyl | 110 |
| 146 | $CH_3$ | $CH_3$ | 6-$CH_3$ | 2 | $CH_2=CH-(CH_2)_8-$ | Oil |
| 147 | $CH_3$ | $CH_3$ | 6-$CH_3$ | 2 | $(H_3C)_2C=C(H_3C)-$ | Oil |
| 148 | $CH_3$ | $CH_3$ | 6-$CH_3$ | 2 | $(CH_3)_3C-CH_2-$ | |

TABLE 2-continued
(Ib)
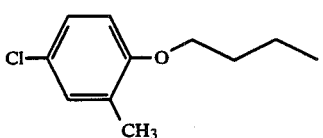
| Example No. | X | Y | $Z_n$ | m | $R^1$ | m.p. °C. |
|---|---|---|---|---|---|---|
| 149 | CH$_3$ | CH$_3$ | 6-CH$_3$ | 2 | 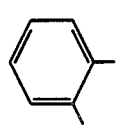 | Oil |
| 150 | CH$_3$ | CH$_3$ | 6-CH$_3$ | 2 | 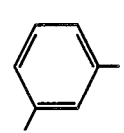 | 118 |
| 151 | CH$_3$ | CH$_3$ | 6-CH$_3$ | 2 | 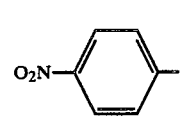 | 147 |
| 152 | CH$_3$ | CH$_3$ | 6-CH$_3$ | 2 | 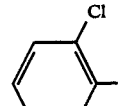 | 88 |
| 153 | CH$_3$ | CH$_3$ | 6-CH$_3$ | 2 | 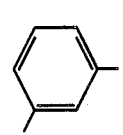 | 75 |
| 154 | CH$_3$ | CH$_3$ | 6-CH$_3$ | 2 | 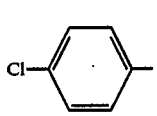 | 98 |
| 155 | CH$_3$ | CH$_3$ | 6-CH$_3$ | 2 | 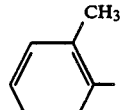 | 117 |
| 156 | CH$_3$ | CH$_3$ | 6-CH$_3$ | 2 | 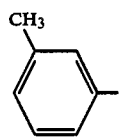 | 84 |
| 157 | CH$_3$ | CH$_3$ | 6-CH$_3$ | 2 |  | 96 |

TABLE 2-continued (Ib)

| Example No. | X | Y | $Z_n$ | m | $R^1$ | m.p. °C. |
|---|---|---|---|---|---|---|
| 158 | $CH_3$ | $CH_3$ | 6-$CH_3$ | 2 | 4-methylphenyl | 125 |
| 159 | $CH_3$ | $CH_3$ | 6-$CH_3$ | 2 | 2-methoxyphenyl | 147 |
| 160 | $CH_3$ | $CH_3$ | 6-$CH_3$ | 2 | 3-methoxyphenyl | 98 |
| 161 | $CH_3$ | $CH_3$ | 6-$CH_3$ | 2 | 4-methoxyphenyl | 102 |
| 162 | $CH_3$ | $CH_3$ | 6-$CH_3$ | 2 | 1-methoxy-1-methylcyclopropyl | 83 |
| 163 | $CH_3$ | $CH_3$ | 6-$CH_3$ | 2 | 2-fluoro-1-methylcyclopropyl | Oil |
| 164 | $CH_3$ | $CH_3$ | 6-$CH_3$ | 2 | 1-chloro-1-methylcyclopropyl (?) (1-chloro cyclopropyl with CH3) | 103 |
| 165 | $CH_3$ | $CH_3$ | 6-$CH_3$ | 2 | 2,2,3-trichloro-3-methylcyclopropyl | Oil |
| 166 | $CH_3$ | $CH_3$ | 6-$CH_3$ | 2 | 2,2-dimethyl-3-(2-methylpropenyl)cyclopropyl | Oil |
| 167 | Cl | Cl | 6-Cl | 2 | $CH_3-$ | 123 |
| 168 | Cl | Cl | 6-Cl | 2 | $(CH_3)_3C-$ | 172 |
| 169 | Cl | $CF_3$ | 6-F | 2 | $(CH_3)_3C-$ | 122 |
| 170 | Cl | $CF_3$ | 6-Cl | 2 | $CH_3-$ | 133 |
| 171 | Cl | $CF_3$ | 6-Cl | 2 | $(CH_3)_3C-$ | 128 |
| 172 | i-$C_3H_7$ | i-$C_3H_7$ | 6-i-$C_3H_7$ | 2 | $CH_3-$ | 125 |
| 173 | i-$C_3H_7$ | i-$C_3H_7$ | 6-i-$C_3H_7$ | 2 | $(CH_3)_3C-$ | 178 |
| 174 | $CH_3$ | F | 6-$CH_3$ | 2 | $CH_3-$ | 85 |
| 175 | $CH_3$ | F | 6-$CH_3$ | 2 | $(CH_3)_3C-$ | 110 |
| 176 | $CH_3$ | $CH_3$ | 6-F | 2 | $CH_3-$ | Oil |

TABLE 2-continued (Ib)

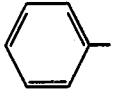

| Example No. | X | Y | $Z_n$ | m | $R^1$ | m.p. °C. |
|---|---|---|---|---|---|---|
| 177 | $CH_3$ | $CH_3$ | 6-F | 2 | $(CH_3)_3C-$ | Oil |
| 178 | $CH_3$ | $t-C_4H_9$ | $6-CH_3$ | 2 | $CH_3-$ | 109 |
| 179 | $CH_3$ | $t-C_4H_9$ | $6-CH_3$ | 2 | $(CH_3)_2CH-$ | 92 |
| 180 | $CH_3$ | $t-C_4H_9$ | $6-CH_3$ | 2 | $(CH_3)_3C-$ | 161 |
| 181 | $CH_3$ | $t-C_4H_9$ | $6-CH_3$ | 2 | $(CH_3)_2CH-C(CH_3)_2-$ | 99 |
| 182 | Cl | H | 3,6-di-Cl | 2 | $CH_3-$ | 127 |
| 183 | Cl | H | 3,6-di-Cl | 2 | $(CH_3)_3C-$ | Oil |
| 184 | $CH_3$ | $CH_3$ | $3,5-di-CH_3$ | 2 | $CH_3-$ | 120 |
| 185 | $CH_3$ | $CH_3$ | $3,5-di-CH_3$ | 2 | $(CH_3)_3C-$ | 107 |
| 186 | $CH_3$ | $CH_3$ | $3,6-di-CH_3$ | 2 | $CH_3-$ | Oil |
| 187 | $CH_3$ | $CH_3$ | $3,6-di-CH_3$ | 2 | $(CH_3)_3C-$ | 97 |
| 188 | $CH_3$ | H | $3,5,6-tri-CH_3$ | 2 | $CH_3-$ | Oil |
| 189 | $CH_3$ | H | $3,5,6-tri-CH_3$ | 2 | $(CH_3)_3C-$ | 82 |
| 190 | $CH_3$ | $CH_3$ | $3-Br,6-CH_3$ | 2 | $CH_3-$ | Oil |
| 191 | $CH_3$ | $CH_3$ | $3-Br,6-CH_3$ | 2 | $(CH_3)_2CH-$ | Oil |
| 192 | $CH_3$ | $CH_3$ | $3-Br,6-CH_3$ | 2 | $(CH_3)_3C-$ | Oil |
| 193 | $CH_3$ | $CH_3$ | $3-Br,6-CH_3$ | 2 | $(CH_3)_2CH-C(CH_3)_2-$ | Oil |
| 194 | $CH_3$ | $CH_3$ | $tri-CH_3$ | 2 | $CH_3-$ | 136 |
| 195 | $CH_3$ | $CH_3$ | $tri-CH_3$ | 2 | $(CH_3)_2CH-$ | 79 |
| 196 | $CH_3$ | $CH_3$ | $tri-CH_3$ | 2 | $(CH_3)_3C-$ | 98 |

TABLE 3

(Ic)

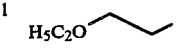

| Example No. | X | Y | $Z_n$ | m | $R^2$ | M.p. °C. |
|---|---|---|---|---|---|---|
| 197 | Cl | Cl | — | 1 | $(CH_3)_2CH-$ | |
| 198 | Cl | Cl | — | 1 | (phenyl) | |
| 199 | Cl | H | 6-Cl | 1 | $CH_3-$ | |
| 200 | Cl | H | 6-Cl | 1 | $(CH_3)_2CH-$ | 115 |
| 201 | Cl | H | 6-Cl | 1 | $(CH_3)_3-C-CH_2-$ | 92 |
| 202 | Cl | H | 6-Cl | 1 | $H_5C_2O-(CH_2)_2-$ | |
| 203 | Cl | H | 6-Cl | 1 | $(CH_3)_2CH-CH_2-$ | Oil |
| 204 | Cl | H | 6-Cl | 1 | $H_3C-(CH_2)_2-CH(CH_3)-$ | Oil |
| 205 | Cl | H | 6-Cl | 1 | $(CH_3)_2CH-CH(CH_3)-$ | 80 |
| 206 | Cl | H | 6-Cl | 1 | $H_5C_2-CH(CH_3)-$ | 46 |

TABLE 3-continued

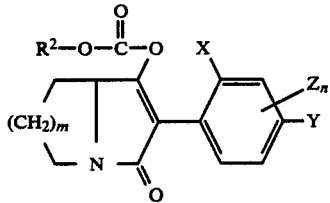

(Ic)

| Example No. | X | Y | $Z_n$ | m | $R^2$ | M.p. °C. |
|---|---|---|---|---|---|---|
| 207 | Cl | H | 6-Cl | 1 | phenyl | |
| 208 | $CH_3$ | $CH_3$ | 5-$CH_3$ | 1 | $(CH_3)_2CH-$ | |
| 209 | $CH_3$ | $CH_3$ | 5-$CH_3$ | 1 | $(CH_3)_2CH-CH_2-$ | |
| 210 | $CH_3$ | $CH_3$ | 5-$CH_3$ | 1 | $H_5C_2-CH(CH_3)-$ | |
| 211 | $CH_3$ | $CH_3$ | 5-$CH_3$ | 1 | $H_5C_2-O-C_2H_4-$ | |
| 212 | $CH_3$ | $CH_3$ | 5-$CH_3$ | 1 | phenyl | |
| 213 | $CH_3$ | $CH_3$ | 6-$CH_3$ | 1 | $CH_3-$ | Oil |
| 214 | $CH_3$ | $CH_3$ | 6-$CH_3$ | 1 | $C_2H_5-$ | Oil |
| 215 | $CH_3$ | $CH_3$ | 6-$CH_3$ | 1 | $(CH_3)CH-$ | 54 |
| 216 | $CH_3$ | $CH_3$ | 6-$CH_3$ | 1 | $(CH_3)_2CH-CH_2-$ | Oil |
| 217 | $CH_3$ | $CH_3$ | 6-$CH_3$ | 1 | $H_5C_2-CH(CH_3)-$ | 95 |
| 218 | $CH_3$ | $CH_3$ | 6-$CH_3$ | 1 | $H_5C_2-O-C_2H_4-$ | Oil |
| 219 | $CH_3$ | $CH_3$ | 6-$CH_3$ | 1 | cyclohexyl-H | Oil |
| 220 | $CH_3$ | $CH_3$ | 6-$CH_3$ | 1 | $(CH_3)_3C-$ | Oil |
| 221 | $CH_3$ | $CH_3$ | 6-$CH_3$ | 1 | $CH_3-(CH_2)_2CH(CH_3)-$ | 98 |
| 222 | $CH_3$ | $CH_3$ | 6-$CH_3$ | 1 | $(CH_3)_3C-CH_2-$ | Oil |
| 223 | $CH_3$ | $CH_3$ | 6-$CH_3$ | 1 | $(CH_3)_2-CH-CH(CH_3)-CH<$ | Oil |
| 224 | Cl | Cl | — | 2 | $(CH_3)_2CH-$ | |
| 225 | Cl | Cl | — | 2 | $(CH_3)_2CH-CH_2-$ | |
| 226 | Cl | Cl | — | 2 | phenyl | |
| 227 | Cl | Cl | — | 2 | $C_2H_5-O-C_2H_4-O-C_2H_4-$ | |
| 228 | Cl | H | 6-Cl | 2 | $H_3C-$ | |
| 229 | Cl | H | 6-Cl | 2 | $(CH_3)_2CH-$ | 121 |
| 230 | Cl | H | 6-Cl | 2 | $(CH_3)_2CHCH_2-$ | 108 |

TABLE 3-continued (Ic)

| Example No. | X | Y | $Z_n$ | m | $R^2$ | M.p. °C. |
|---|---|---|---|---|---|---|
| 231 | Cl | H | 6-Cl | 2 | $H_5C_2-CH(CH_3)-$ | 100 |
| 232 | Cl | H | 6-Cl | 2 | $H_5C_2-O-CH_2CH_2CH_2-$ | Oil |
| 233 | Cl | H | 6-Cl | 2 | $H_5C_2-O-CH_2CH_2-O-CH_2CH_2CH_2-$ | Oil |
| 234 | Cl | H | 6-Cl | 2 | phenyl- | 138 |
| 235 | $CH_3$ | $CH_3$ | 5-$CH_3$ | 2 | $H_3C-$ | |
| 236 | $CH_3$ | $CH_3$ | 5-$CH_3$ | 2 | $(CH_3)_2CH-$ | |
| 237 | $CH_3$ | $CH_3$ | 5-$CH_3$ | 2 | $(CH_3)_2CH-CH_2-$ | |
| 238 | $CH_3$ | $CH_3$ | 5-$CH_3$ | 2 | $H_5C_2-CH(CH_3)-$ | |
| 239 | $CH_3$ | $CH_3$ | 5-$CH_3$ | 2 | $H_5C_2-O-CH_2CH_2CH_2-$ | |
| 240 | $CH_3$ | $CH_3$ | 5-$CH_3$ | 2 | phenyl- | |
| 241 | $CH_3$ | $CH_3$ | 6-$CH_3$ | 2 | $H_3C-$ | 105 |
| 242 | $CH_3$ | $CH_3$ | 6-$CH_3$ | 2 | $C_2H_5-$ | 102 |
| 243 | $CH_3$ | $CH_3$ | 6-$CH_3$ | 2 | $(CH_3)_2CH-$ | Oil |
| 244 | $CH_3$ | $CH_3$ | 6-$CH_3$ | 2 | $(CH_3)_2CH-CH_2-$ | Oil |
| 245 | $CH_3$ | $CH_3$ | 6-$CH_3$ | 2 | $H_5C_2-CH(CH_3)-$ | Oil |
| 246 | $CH_3$ | $CH_3$ | 6-$CH_3$ | 2 | $H_5C_2-O-CH_2CH_2CH_2-$ | Oil |
| 247 | $CH_3$ | $CH_3$ | 6-$CH_3$ | 2 | $H_5C_2-O-CH_2CH_2-O-CH_2CH_2CH_2-$ | Oil |
| 248 | $CH_3$ | $CH_3$ | 6-$CH_3$ | 2 | phenyl- | 110 |
| 249 | $CH_3$ | $CH_3$ | 6-$CH_3$ | 2 | $(CH_3)_3C-$ | 109 |
| 250 | $CH_3$ | $CH_3$ | 6-$CH_3$ | 2 | $CH_3-(CH_2)_2-CH(CH_3)-$ | Oil |
| 251 | $CH_3$ | $CH_3$ | 6-$CH_3$ | 2 | $(CH_3)_2CH-CH(CH_3)-$ | Oil |
| 252 | $CH_3$ | $CH_3$ | 6-$CH_3$ | 2 | $(CH_3)_3C-CH_2-$ | Oil |

TABLE 3-continued (Ic)

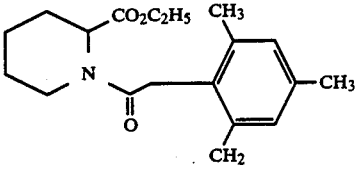

| Example No. | X | Y | $Z_n$ | m | $R^2$ | M.p. °C. |
|---|---|---|---|---|---|---|
| 253 | CH$_3$ | CH$_3$ | 6-CH$_3$ | 2 | cyclohexyl | 142 |
| 254 | CH$_3$ | t-C$_4$H$_9$ | — | 2 | C$_2$H$_5$—CH(CH$_3$)— | Oil |
| 255 | CH$_3$ | F | 6-CH$_3$ | 2 | (CH$_3$)$_2$CH— | Oil |

EXAMPLE 256

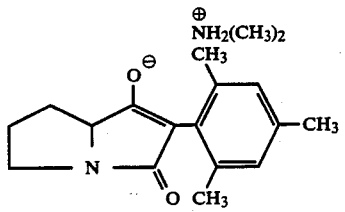

2.57 g (10 mmol) of 3-(2,4,6-trimethyl-phenyl)-1,5-trimethylene-pyrrolidine-2,4-dione are suspended in 50 ml of absolute THF (tetrahydrofuran), and dimethylamine is subsequently passed through until gas is taken up no longer. After the THF has been removed on a rotary evaporator, the residue is dried in vacuo at 70° C. Yield: 2.69 g (89.7% of theory) m.p. 62° C.

In a corresponding manner, compounds of the formula (Id) were prepared:

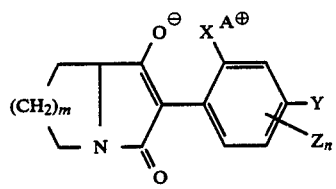

(Id)

TABLE 4

| Example No. | X | Y | $Z_n$ | m | A$^\oplus$ | M.p. °C. |
|---|---|---|---|---|---|---|
| 257 | CH$_3$ | CH$_3$ | CH$_3$ | 1 | Na$^\oplus$ | <230 |
| 258 | CH$_3$ | CH$_3$ | CH$_3$ | 1 | NH$_3^\oplus$ | 228 |

INTERMEDIATES EXAMPLE 5'

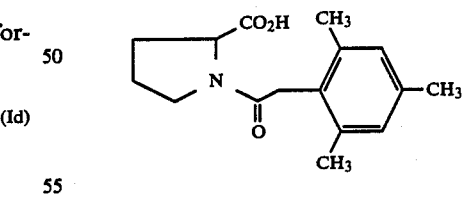

223 g (1.125 mol) of mesityleneacetyl chloride are added dropwise at 0° to 10° C. to 182 ml (1.157 mol) of ethyl pipecolinate and 162 ml (1.157 mol) of triethylamine in 1,200 ml of absolute tetrahydrofuran (THF), followed by stirring for 1 hour at room temperature. After the mixture has been stirred into 5 liters of ice water and 500 ml of 1 N HCl, the product is filtered off with suction, washed with water and dried in vacuo at 50° C. over P$_2$O$_5$. 342.3 g (95.2% of theory) of ethyl N-(2,4,6-trimethylphenylacetyl)-piperidine-2-carboxylate are obtained.

EXAMPLE 37'

20 g (0.5 mol) of NaOH pellets are added to 115 g (1 mol) of L-proline in 1 liter of water. 60 g (1.5 mol) of NaOH in 300 ml of water and 197.6 g (1 mol) of mesityleneacetyl chloride are added dropwise in a synchronous manner at a temperature of less than 40° C., followed by stirring for 1 hour. The mixture is subsequently acidified at 5° to 20° C. using concentrated hydrochloric acid, and the product is filtered off with suction and dried in vacuo at 70° C. over P$_2$O$_5$.

Yield: 262 g (95.3% of theory) of N-2,4,6-trimethylphenylacetylproline m.p. 156° C.

EXAMPLE 26'

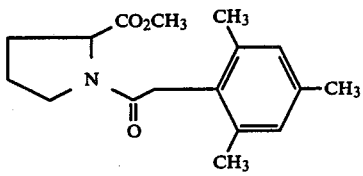

137.5 g (0.5 mol) of N-2,4,6-trimethylphenylacetyl-proline are dissolved in 500 mol of methanol. After 73 ml (0.55 mol) of dimethoxypropane and 4.75 g (25 mmol) of p-toluenesulphonic acid monohydrate have been added, the mixture is refluxed for 2 hours. After the mixture has been evaporated on a rotary evaporator, the residue is taken up in methylene chloride and washed using sodium hydrogen carbonate solution, and the methylene chloride phase is dried and evaporated on a rotary evaporator. After the residue had been recrystallized from methylene chloride/methyl-tert.-butyl ether/n-hexane, 107.9 g (74.7%) of methyl N-(2,4,6-trimethylphenylacetyl)-pyrrolidine-2-carboxylate were obtained. M.p. 74° C.

The active compounds are suitable for combating animal pests, preferably arthropods and nematodes, in particular insects and arachnids, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa spp., Locusta migratoria migratorioides, Melanoplus differentialis* and *Schistocerca gregaria.*

From the order of the Dermaptera, for example, *Forficula auricularia.*

From the order of the Isoptera, for example, *Reticulitermes spp.*

From the order of the Anoplura, for example, *Phylloxera vastatrix, Pemphigus spp., Pediculus humanus corporis, Haematopinus spp.* and *Linognathus spp.*

From the order of the Mallophaga, for example, *Trichodectes spp.* and *Damalinea spp.*

From the order of the Thysanoptera, for example, *Hercinothrips femoralis* and *Thrips tabaci.*

From the order of the Heteroptera, for example, *Eurygaster spp., Dysdercus intermedius, Piesma quadrata, Cimex lectularius, Rhodnius prolixus* and *Triatoma spp.*

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp.* and *Psylla spp.*

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis* and *Costelytra zealandica.*

From the order of the Hymenoptera, for example, *Diprion spp., Hoplocampa spp., Lasius spp., Monomorium pharaonis* and *Vespa spp.*

From the order of the Diptera, for example, *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae* and *Tipula paludosa.*

From the order of the Siphonaptera, for example, *Xenopsylla cheopis* and *Ceratophyllus spp.*

From the order of the Arachnida, for example, *Scorpio maurus* and *Latrodectus mactans.*

From the order of the Acarina, for example, *Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp.* and *Tetranychus spp.*

The phytoparasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp.* and *Trichodorus spp.*

The active compounds according to the invention can furthermore be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

It is characteristic of the compounds according to the invention that they have a selective activity against monocotyledon weeds when used in the pre- and post-emergence method, while being well tolerated by crop plants.

The active compounds according to the invention can be used, for example, in connection with the following plants:

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this context, the active compounds according to the invention not only have an excellent action against noxious plants but are also well tolerated by important crop plants, such as, for example, wheat, cotton, soya beans, citrus fruit and sugar beet, and they can therefore be used as selective weedkillers.

The active compounds can be converted into the customary formulations, such as solutions, emulsions, powders, foams, suspensions, pastes, granules, aerosols, natural and synthetic materials impregnated with active compound, very fine capsules in polymeric substances and in coating compositions for seed, furthermore in formulations using burning equipment, such as fumigating cartridges, fumigating cans, fumigating spirals and the like, as well as ULV cold-mist and warm-mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; liquefied gaseous extenders or carriers are taken to mean those liquids which are gaseous at normal temperatures and under atmospheric pressure, for example, aerosol propellant, such as halogenohydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foamforming agents there are suitable: for example, non-ionic and anionic emulsifiers, such as polyoxyethylene fatty acid esters, polyoxyethylene fatty alcohol ethers, for example, alkylaryl polyglycol ethers, alkylsulphonates, alkyl sulphates, arylsulphonates and well as albumen hydrolysis products; as dispersing agents there are suitable: for example, ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, herbicides or fungicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.001 and 1% by weight.

The compounds are employed in a customary manner appropriate for the use forms.

The active compounds which can be used according to the invention are also suitable for combating mites, ticks etc. in the sector of animal keeping and cattle breeding; better results, for example higher milk production, greater weight, more attractive animal pelt, longer lift etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form, for example, of injection, and, furthermore, by means of the feed-through process. In addition, application as moulded articles (collar, ear tag) is also possible.

The compounds of the formula (I) according to the invention show antimicrobial, in particular powerful antibacterial antimycotic, actions. They possess a very broad spectrum of antimycotic action, in particular against Dermatophytes and Blastomycetes, and biphasic fungi, for example against Candida species, such as *Candida albicans*, Epidermophyton species, such as *Epidermophyton floccosum*, Aspergillus species, such as *Aspergillus niger* and *Aspergillus fumigatus*, Trichophyton species, such as *Trichophyton mentagrophytes*, Microsporon species, such as *Microsporon felineum*, and also Torulopsis species, such as *Torulopsis glabrata*. The enumeration of these microorganisms in no case represents a limitation of the germs which can be combated, but is only of illustrative character.

Examples of indications in human medicine which may be mentioned are:

Dermatomycoses and systemic mycoses caused by *Trichophyton mentagrophytes* and other Trichophyton species, Microsporon species and also *Epidermophyton floccosum*, Blastomycetes and biphasic fungi, and moulds.

Indication areas which may be mentioned in veterinary medicine by way of example are: All dermatomycoses and systemic mycoses, in particular those caused by the abovementioned pathogens.

The present invention includes pharmaceutical preparations which contain, beside non-toxic, inert pharmaceutically suitable excipients, one or more active compounds according to the invention, or which consist of one or more active compounds according to the invention.

The present invention also includes pharmaceutical preparations in dosage units. This means that the preparations are present in the form of individual portions, for example tablets, coated tablets, capsules, pills, suppositories and ampoules, whose active compound content corresponds to a fraction or a multiple of an individual dose. The dosage units may contain, for example 1, 2, 3 or 4 individual doses or $\frac{1}{2}$, $\frac{1}{3}$ or $\frac{1}{4}$ of an individual dose. An individual dose preferably contains the amount of active compound which is administered in one application and which usually corresponds to a whole, a half or a third or a quarter of a daily dose.

Non-toxic, inert, pharmaceutically suitable excipients are taken to mean solid, semi-solid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules may contain the active compound(s) in addition to the customary excipients, such as (a) fillers and extenders, for example, starches, lactose, sucrose, glucose, mannitol and silica, (b) binders, for example carboxymethylcellulose, alginates, gelatin, polyvinylpyrrolidone, (c) humectants, for example, glycerol, (d) disintegrants, for example, agar-agar, calcium carbonate and sodium bicarbonate, (e) solution retardants, for example, paraffin, and (f) absorption accelerators, for example, quaternary ammonium compounds, (g) wetting agents, for example cetyl alcohol, glycerol monostearate, (h) adsorption agents, for example, kaolin and bentonite, and (i) lubricants, for example, talc, calcium stearate and magnesium stearate and solid polyethylene glycols or mixtures of the substances mentioned under (a) to (i).

The tablets, coated tablets, capsules, pills and granules may be provided with the customary coatings and shells, which may optionally contain opacifying agents, and they can be composed such that they release the active compound(s) only, or preferably, in a certain part of the intestinal tract, if appropriate in a slow-release manner, examples of embedding materials which can be used being polymeric substances and waxes.

If appropriate, the active compound(s) can also be in a microencapsulated form together with one or more of the abovementioned excipients.

In addition to the active compound(s), suppositories may contain the customary water-soluble or water-insoluble excipients, for example polyethylene glycols, fats, for example cocoa fat, and higher esters (for example $C_{14}$-alcohol with $C_{16}$-fatty acid) or mixtures of these substances.

Ointments, pastes, creams and gels may contain, besides the active compound(s), the customary excipients, for example animal and vegetable fats, waxes, paraffins, starch, tragacanth, cellulose derivatives, polyethylene glycols, silicones, bentonites, silica, talc and zinc oxide or mixtures of these substances.

Powders and sprays may contain, besides the active compound(s), the customary excipients, for example, lactose, talc, silica, aluminium hydroxide, calcium silicate and polyamide powder or mixtures of these substances, and sprays may additionally contain the customary propellants, for example, chlorofluoro hydrocarbons.

Solutions and emulsions may contain, besides the active compound(s), the customary excipients, such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycols and fatty acid esters of sorbitan or mixtures of these substances.

For parenteral application, the solutions and emulsions can also be present in sterile and blood-isotonic forms.

Suspensions can contain, besides the active compound(s), the customary excipients, such as liquid diluents, for example, water, ethyl alcohol, propyl alcohol, suspending agents, for example, ethoxylated isostearyl alcohols, polyoxyethylene sorbitol esters and polyoxyethylene sorbitan esters, microcrystalline cellulose, aluminium metahydroxide, bentonite, agar-agar and tragacanth or mixtures of these substances.

The said formulation forms may also contain colorants, preservatives and odor- and flavor-improving additives, for example, peppermint oil and eucalyptus oil, and sweeteners, for example, saccharin.

The therapeutically active compounds should preferably be present in the abovementioned pharmaceutical preparations in a concentration of about 0.1 to 99.5, preferably of 0.5 to 95, % by weight of the total mixture.

The pharmaceutical preparations indicated above can also contain further pharmaceutical active compounds in addition to the active compounds according to the invention.

The pharmaceutical preparations indicated above are prepared in a customary manner by known methods, for example by mixing the active compound(s) with the excipients(s).

The present invention also includes the use of the active compounds according to the invention, and that of the pharmaceutical preparations containing one or more active compounds according to the invention, in human and veterinary medicine for the prophylaxis, amelioration and/or cure of the diseases indicated above.

The active compounds or the pharmaceutical preparations can be administered locally, orally, parenterally, intraperitoneally and/or rectally, preferably parenterally, in particular intravenously.

In general, it has proved advantageous both in human and in veterinary medicine to administer the active compound(s) according to the invention in total amounts of about 2.5 to about 200, preferably from 5 to 150, mg/kg of body weight every 24 hours, if appropriate in the form of several individual doses, to obtain the desired results.

For oral administration, the active compounds according to the invention are administered in total amounts of about 2.5 to about 200, preferably of 5 to 150, mg/kg of body weight every 24 hours, and for parenteral application in total amounts of about 2.5 to about 50, preferably of 1 to 25, mg/kg of body weight every 24 hours.

It may be necessary, however, to deviate from the said dosages, depending upon the nature and the body weight of the subject to be treated, the nature and severity of the disease, the nature of the preparation and the administration of the medicament and also the period or interval within which the administration takes place. Thus, in some cases it may be sufficient to manage with less than the abovementioned amount of active compound, while in other cases the amount of active compound indicated above must be exceeded. The optimum dosage required in each case and the nature of administration of the active compounds can easily be established by anyone skilled in the art on the basis of his expert knowledge.

EXAMPLE A Tetranychus test (resistant)

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the common spider mite or bean spider mite (*Tetranychus urticae*) are treated by being dipped into the active compound preparation of the desired concentration.

After the desired time the destruction is determined in %. 100% here denotes that all spider mites have been destroyed; 0% denotes that none of the spider mites have been destroyed.

In this test, for example, the following compounds of the Preparation Examples show a superior activity compared with the prior art (88).

EXAMPLE B Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)
100%=total destruction

In this test, for example, the following compounds of the Preparation Examples show a superior activity compared with the prior art: (1), (13).

EXAMPLE C Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, for example, the following compounds of the Preparation Examples show a superior activity compared with the prior art: (1), (13).

EXAMPLE D Test with *Lucilia cuprina* resistant larvae

Solvent:
35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 *Lucilia cuprina* resistant larvae are introduced into a test tube which contains approx. 1 cm³ of horse meat and 0.5 ml of the preparation of active compound. After 24 hours, the degree of destruction is determined.

In this test, for example, the following compounds of the Preparation Examples show a highly pronounced activity: 7, 54, 58, 62, 64, 67, 68, 213, 215, 216, 217, 222.

EXAMPLE E Test with *Psoroptes ovis*

Emulsifier:
35 parts by weight of ethylene glycol monomethyl ether
35 parts by weight of nonylphenol polyglycol ether To produce a suitable preparation of active compound, three parts by weight of active compound are mixed with seven part by weight of the abovementioned mixture, and the concentrate thus obtained is diluted with water to the desired concentration.

About 10–25 *Psoroptes ovis* are introduced into 1 ml of the active compound preparation to be tested, which has been pipetted into tablet nests of a deep-drawn pack. After 24 hours, the degree of destruction is determined.

In this test, for example, the following compounds of the Preparation Examples show a highly pronounced activity: 39, 55, 57, 62, 87, 89, 167, 201, 245.

EXAMPLE F Antimycotic in vitro activity

Description of the test:

The in vitro tests were carried out using microorganism inocular having an average of $1 \times 10^4$ microorganisms/ml of substrate. The nutrient medium used was Yeast Nitrogen Base medium for yeasts and Kimmig medium for moulds and Dermatophytes.

The incubation temperature was 37° C. in the case of the yeasts and 28° C. in the case of molds and Dermatophytes, the incubation time was 24 to 96 hours for yeasts and 96 to 120 hours for Dermatophytes and molds.

The fungicides were assessed by plating and reincubation of completely inhibited batches, fungicidal concentrations being those which contain fewer than 100 microorganisms c.f.n. (colony-forming unit) per ml.

In this test, the compounds of the formula (I) according to the invention, of the Preparation Examples 36, 40, 85, 91, 114, 116, 120, 167, 170, 174, 176, 178, 182, 184, 188, 194 show a highly pronounced antimycotic activity.

It will be appreciated that the instant specification and claims are set forth by way of illustration and not limitation, and that various modifications and changes may be made without departing from the spirit and scope of the present invention.

What is claimed is:

1. A compound of the formula (I)

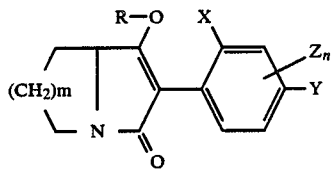

in which
X represents alkyl and halogen,
Y represents hydrogen, alkyl, halogen and halogenoalkyl,
Z represents alkyl and halogen,
m represents a number from 1–4,
n represents a number from 0–3,
R represents hydrogen, —COR¹,

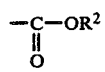

or A, where
A represents a metal cation equivalent or represents an ammonium ion.
R¹ represents a metal cation equivalent or represents an ammonium ion,
R¹ represents unsubstituted or halogen-substituted alkyl, alkenyl, alkoxyalkyl, alkythioalkyl, polyalkoxyalkyl and unsubstituted cycloalkyl having 3 to 8 ring atoms and being uninterrupted by hetero atoms or being interrupted in the ring by oxygen and/or sulfur, or R¹ represents unsubstituted phenyl or phenyl substituted by halogen, nitro, $C_1$–$C_6$-alkyl, $C_1$–$C_6$-halogenoalkoxy or $C_1$–$C_6$-halogenoalkyl, unsubstitued phenylalkyl or phenyalkyl substituted by halogen, $C_1$–$c_6$-alkyl, $C_1$–$C_6$-alkoxy, $C_1$–$C_6$-halogenoalkyl or $C_1$–$C_6$-halogenoalkoxy, unsubstituted pyridyl, pyrimidyl, thiazolyl or pyrazolyl, or pyridyl, pyrimidyl, thiazolyl or pyrazolyl substituted by halogen or $C_1$–$C_6$-alkyl and unsubstituted or halogen, amino or $C_1$–$C_6$-alkyl-substituted pyridyloxy-$C_1$–$C_6$-alkyl, pyrimidyloxy-$C_1$–$C_8$-alkyl or -thiazolyloxy-$C_1$–$C_6$-alkyl, and
R² represents unsubstituted or halogen-substituted alkyl, cycloalkyl, alkenyl, alkoxyalkyl, polyalkoxyalkyl and unsubstituted phenyl or phenyl substituted by halogen, $C_1$–$C_6$-alkyl, $C_1$–$C_6$-alkoxy or $C_1$–$C_6$-halogenoalkyl, as well as the pure enantiomeric forms of the compounds of the formula (I).

2. A compound of the formula (I) according to claim 1, in which
X represents $C_1$–$C_6$-alkyl and halogen
Y represents hydrogen, $C_1$–$C_6$-alkyl, halogen and $C_1$–$C_3$-halogenoalkyl
Z represents $C_1$–$C_6$-alkyl and halogen,
m represents a number from 1–4,
n represents a number from 0–3,
R represents hydrogen, —CO—R¹, —CO—O—R² or A, in which
A represents a metal cation equivalent or represents an ammonium ion,
R¹ represents unsubstituted or halogen-substituted: $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl and cycloalkyl which has 3–8 ring atoms and which is uninterrupted by hetero atoms or is interrupted in the ring by oxygen and/or sulphur, or represents unsubstituted phenyl or phenyl substituted by halogen, nitro, $C_1$–$C_6$-alkyl, $C_1$–$C_6$-halogenoalkoxy or $C_1$–$C_6$-halogenoalkyl;
or represents unsubstituted phenyl-$C_1$–$C_6$-alkyl or phenyl-$C_1$–$C_6$-alkyl substituted by halogen, $C_1$–$C_6$-alkyl, $C_1$–$C_6$-alkoxy, $C_1$–$C_6$-halogenoalkyl or $C_1$–$C_6$-halogenoalkoxy, or $R^1$ represents unsubstituted pyridyl, pyrimidyl, thiazolyl or pyrazolyl or pyridyl, pyrimidyl, thiazolyl or pyrazolyl substituted by halogen or $C_1$–$C_6$-alkyl, $R^1$ represents unsubstituted phenoxy-$C_1$–$C_6$-alkyl or phenoxy-$C_1$–$C_6$-alkyl substituted by halogen or $C_1$–$C_6$-alkyl, or represents unsubstituted or halogen, amino or $C_1$–$C_6$-alkyl substituted pyrimidyloxy-$C_1$–$C_6$-alkyl, pyrimidyloxy-$C_1$–$C_6$-alkyl or thiazolyloxy-$C_1$–$C_6$-alkyl, $R^2$ represents unsubstituted or halogen substituted: $C_1$–$C_{20}$-alkyl, $C_2$–$C_{20}$-alkenyl, $C_1$–$C_8$-alkoxy-$C_2$–$C_8$-alkyl and $C_1$–$C_8$-polyalkoxy-$C_2$–$C_8$-alkyl, or $R^2$ represents halogen-, $C_1$–$C_6$-alkyl-, $C_1$–$C_6$-alkoxy- or $C_1$–$C_6$-halogenoalkyl-substituted phenyl, and enantiomeric forms thereof.

3. A compound of the formula (I) according to claim 1, in which

X represents $C_1$–$C_4$-alkyl and halogen,

Y represents hydrogen, $C_1$–$C_6$-alkyl, halogen and $C_1$–$C_2$-halogenoalkyl, Z represents $C_1$–$C_4$-alkyl and halogen, alkyl, pyrimidyloxy-$C_1$–$C_6$-alkyl or thiazolyloxy-$C_1$–$C_6$-alkyl, m represents a number from 1–3, n represents a number from 0–3, R represents hydrogen, —CO—$R^1$, —CO—O—$R^2$ or A, in which A represents a metal cation equivalent or represents an ammonium ion, $R^1$ represents unsubstituted or halogen-substituted: $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_2$–$C_6$-alkyl and cycloalkyl which has 3–7 ring atoms and which is uninterrupted by a hetero atom or interrupted by 1–2 oxygen and/or sulphur atoms in the ring, or represents unsubstituted or halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents unsubstituted or halogen- or $C_1$–$C_6$-alkyl-substituted pyridyl, pyrimidyl, thiazolyl or pyrazolyl, or represents unsubstituted or halogen- or $C_1$–$C_4$-alkyl-substituted phenoxy-$C_1$–$C_5$-alkyl, or represents unsubstituted or halogen-, amino- and $C_1$–$C_4$-alkyl-substituted hetaryloxy-$C_1$–$C_5$-alkyl, $R^2$ represents unsubstituted or halogen-substituted: $C_1$–$C_{16}$-alkyl, $C_2$–$C_{16}$-alkenyl, $C_1$–$C_6$-alkoxy-$C_2$–$C_6$-alkyl or $C_1$–$C_6$-polyalkoxy-$C_2$–$C_6$-alkyl, or represents unsubstituted or halogen-, $C_1$–$C_4$-alkyl-, $C_1$–$C_3$-alkoxy- or $C_1$–$C_3$-halogenoalkyl-substituted phenyl, and enantiomerically pure forms thereof.

4. A compound of the formula (I) according to claim 1, in which

X represents methyl, ethyl, propyl, i-propyl, fluorine, chlorine and bromine,

Y represents hydrogen, methyl, ethyl, propyl, i-propyl, butyl, i-butyl, tert.-butyl, chlorine, bromine and trifluoromethyl, Z represents methyl, ethyl, i-propyl, butyl, i-butyl, tert.-butyl, chlorine and bromine, m represents a number from 1–2, n represents a number from 0–3, R represents hydrogen, —CO—$R^1$, —CO—O—$R^2$ or a, in which a represents a metal cation equivalent or an ammonium ion, $R^1$ represents unsubstituted or fluorine- or chlorine-substituted: $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxyl-$C_2$–$C_4$-alkyl and cycloalkyl which has 3–6 ring atoms and which is uninterrupted by hetero atoms or interrupted by 1–2 oxygen and/or sulphur atoms in the ring, or represents unsubstituted or fluorine-, chlorine-, bromine-, methyl-, ethyl-, propyl-, i-propyl-, methoxy-, ethoxy-, trifluoromethyl-, trifluoromethoxy-, or nitro-substituted phenyl, or represents unsubstituted or fluorine-, chlorine-, bromine-, methyl-, ethyl-, propyl-, i-propyl-, methoxy-, ethoxy-, trifluoromethyl- or trifluoromethoxy-substituted phenyl-$C_1$–$C_3$-alkyl, or represents unsubstituted or fluorine-, chlorine, bromine-, methyl- or ethyl-substituted pyridyl, pyrimidyl, thiazolyl and pyrazolyl, or represents unsubstituted or fluorine, chlorine-, methyl- or ethyl-substituted phenoxy-$C_1$–$C_4$-alkyl, or represents unsubstituted or fluorine-, chlorine-, amino-, methyl- or ethyl-substituted pyridyloxy-$C_1$–$C_4$-alkyl, pyrimidyloxy-$C_1$–$C_4$-alkyl and thiazolyloxy-$C_1$–$C_4$-alkyl, $R^2$ represents unsubstituted or fluorine- or chlorine-substituted: $C_1$–$C_{14}$-alkyl, $c_2$–$C_{14}$-alkenyl, $C_1$–$C_4$-alkoxy-$C_2$–$C_6$-alkyl and $C_1$–$C_4$-polyalkoxy-$C_2$–$C_6$-alkyl, or represents unsubstituted or fluorine-, chlorine-, methyl-, ethyl-, propyl-, i-propyl-, methoxy-, ethoxy- or trifluoromethyl-substituted phenyl, and enantiomerically pure forms thereof.

5. An insecticidal and/or acaricidal and/or herbicidal composition comprising an insecticidal and/or acaricidal and/or herbicidal effective amount of at least one compound of the formula (I) according to claim 1 in admixture with a diluent.

6. A method of combating insects and/or arachnids and/or weeds, comprising applying an insecticidal and/or acaricidal and/or herbicidal effective amount of a compound of the formula according to claim 1 to insects and/or arachnids and/or weeds and/or their environment.

* * * * *

UNITED STATES PATENT AND TRADEMARK OFFICE
CERTIFICATE OF CORRECTION

PATENT NO. : 4,985,063

DATED : January 15, 1991

INVENTOR(S) : Fischer et al.

It is certified that error appears in the above-identified patent and that said Letters Patent is hereby corrected as shown below:

Col. 48, lines 17-18   Delete " R' represents a metal cation equivalent or represents an ammonium ion, "

Col. 48, line 21   After " cycloalkyl " insert -- or halogen-substituted cycloalkyl, the cycloalkyl --

Signed and Sealed this

Sixth Day of October, 1992

Attest:

DOUGLAS B. COMER

*Attesting Officer*   Acting Commissioner of Patents and Trademarks